United States Patent [19]

Hammer et al.

[11] Patent Number: 5,545,757
[45] Date of Patent: Aug. 13, 1996

[54] PRODUCTION OF ETHANOLAMINES

[75] Inventors: Hans Hammer, Mannheim; Werner Reutemann, Bobenheim-Roxheim, both of Germany

[73] Assignee: BASF Aktiengesellschaft, Ludwigshafen, Germany

[21] Appl. No.: 413,128

[22] Filed: Mar. 17, 1995

[30] Foreign Application Priority Data

Mar. 26, 1994 [DE] Germany .................. 44 10 610.6

[51] Int. Cl.⁶ .................................. C07C 209/60
[52] U.S. Cl. ................ 564/475; 564/477; 564/503; 564/506
[58] Field of Search ................... 564/477, 475, 564/503, 506

[56] References Cited

U.S. PATENT DOCUMENTS 3,723,530 3/1973 Goetze et al. .................. 564/477
4,939,301 7/1990 Grice et al. .................... 564/477

OTHER PUBLICATIONS

Chemical Abstracts 96 (1982) 51806g.

*Primary Examiner*—Brian M. Burn
*Attorney, Agent, or Firm*—John H. Shurtleff

[57] ABSTRACT

A process for producing mixtures of mono-, di- and triethanol-amine by reacting ammonia and ethylene oxide in a cooled tubular reactor at temperatures from 110° to 160° C. and pressures from 50 to 120 bar comprises using ammonia and ethylene oxide in a molar ratio from 1:1 to 100:1 and ammonia in the form of a from 60 to 99.99% strength aqueous solution and adding from 1 to 80% of the ethylene oxide in from one to ten aliquots over from 10 to 70% of the total length of the tubular reactor.

10 Claims, No Drawings

PRODUCTION OF ETHANOLAMINES

The present invention relates to a process for producing mixtures of mono-, di- and triethanolamines by reacting ammonia and ethylene oxide in a cooled tubular reactor by adding the ethylene oxide in one or more aliquots.

It is common knowledge that ethanolamines can be produced by reaction between ammonia and ethylene oxide at elevated temperatures and pressures. Ammonia is preferably used in the form of an aqueous solution, the water acting as catalyst. Since the reaction system is one of competing consecutive reactions, it produces monoethanolamine, diethanolamine and triethanolamine simultaneously.

Chem. Abstr. 96 (1982), 51806 g, discloses a process for producing alkanolamines from alkylene oxides using an excess of a from 5 to 50% strength by weight ammonia solution at temperatures from 30° to 100° C. and at pressures from 3 to 40 bar. This process involves from 2 to 7 adiabatically operated tubular reactors with cooling downstream of each reactor. The disadvantages of this process are the high water content of the reaction mixture, the low reaction temperature and the resulting long residence times.

It is an object of the present invention to remedy the aforementioned disadvantages.

We have found that this object is achieved by a novel and improved process for producing mixtures of mono-, di- and triethanolamine by reacting ammonia and ethylene oxide in a cooled tubular reactor at temperatures from 110° to 150° C. and pressures from 50 to 120 bar, which comprises using ammonia and ethylene oxide in a molar ratio from 1:1 to 100:1 and ammonia in the form of a from 60 to 99.99% strength aqueous solution and adding from 1 to 80% of the ethylene oxide in from one to ten aliquots over from 10 to 70% of the total length of the tubular reactor.

The present invention can be carried out as follows:

From 20 to 99% by weight, preferably from 40 to 95% by weight, particularly preferably from 50 to 90% by weight, of the total ethylene oxide is mixed with the total ammonia in from 60 to 99.99% strength, preferably from 65 to 99% strength, particularly preferably from 70 to 95% strength, aqueous solution upstream of the cooled tubular reactor, preferably a tubular reactor with jacket cooling, preferably preheated to temperatures from 40 to 70° C., and introduced into the reactor, and the remaining ethylene oxide from 1 to 80% by weight, preferably from 5 to 60% by weight, particularly preferably from 10 to 50% by weight, is mixed into the ammonia in aqueous solution, or the reaction mixture, in one or more, for example from one to ten portions, preferably from one to eight, particularly preferably from one to six, portions divided over from 10 to 70%, preferably from 20 to 60%, particularly preferably from 25 to 50%, of the total length of the tubular reactor.

The reaction temperature in the tubular reactor is generally not more than 160° C., such as from 110° to 160° C., preferably from 120° to 150° C., and the reaction pressure is generally from 50 to 120 bar, preferably from 60 to 110 bar, particularly preferably from 75 to 100 bar.

The molar ratio of ammonia to ethylene oxide can vary within wide limits; generally it is from 1:1 to 100:1, preferably from 3:1 to 50:1, particularly preferably from 4:1 to 25:1.

The reaction can preferably be carried out without an ion exchanger as catalyst.

Generally, in the process of the invention, the ethylene oxide will have completely or substantially reacted before the next portion of ethylene oxide is added to the mixture of ammonia in aqueous solution and the reaction product (mixture of monoethanolamine, diethanolamine, triethanolamine).

The number of portions into which the ethylene oxide is divided and the size of the individual portions is optional, depending only on the design of the reactor (for example: division into 2 portions in a weight ratio of 60:40; or 3 portions in a weight ratio of 60:20:20, or 5 portions in a weight ratio of 50:20:10:10:10).

Control of the proportions of monoethanolamine, diethanolamine and triethanolamine is generally possible by varying the molar ratio of ammonia to ethylene oxide. A high molar excess of ammonia to ethylene oxide generally results in the formation of a high proportion of monoethanolamine.

If the molar excess of ammonia relative to ethylene oxide is reduced, the proportion of diethanolamine and triethanolamine in the reaction product generally increases considerably at the expense of the monoethanolamine.

The velocity of flow through the tubular reactor is generally chosen in such a way as to ensure a turbulent flow regime (avoidance of back mixing, better heat transfer). It is generally necessary to prevent the formation of two phases (diphasicness). The proviso that the reaction is to be carried out in homogeneous liquid phase requires the existence at all times of a minimum pressure which is somewhat greater than the vapor pressure of the reaction mixture at the chosen temperature. Significantly higher pressures than the minimum pressures do not result in disadvantages, but they are not necessary either.

High reaction temperatures above 170° C. have the disadvantage that the workup gives rise to pure products (monoethanolamine, diethanolamine, triethanolamine) which are not color-stable, ie. which discolor in the course of storage.

The reaction is very rapid. The residence time required for complete conversion generally ranges from 1 to 40 minutes, and can be shortened by raising the reaction temperature and the water concentration.

To prevent excessive heating of the reaction product, the reaction mixture can be diluted with water or ammonia. However, removal of the ammonia or water in the course of the workup requires a great deal of energy. Another way of limiting the maximum reaction temperature is to reduce the throughput through the reactor. This reduces the heat of reaction evolved per unit time. However, it greatly limits the capacity of the reactor.

It is advantageous to cool the reaction product to such an extent (down to 100°–140° C.) before the addition of a new portion of ethylene oxide that, although the reaction will take place immediately, the increase in temperature due to the heat of reaction does not have the effect of heating the reaction product to above 150° C. or to such an extent that diphasicness occurs.

The process of the invention makes it possible to divide the reaction between ethylene oxide and ammonia into individual sections. The exchange of energy is facilitated, and the maximum reaction temperature is significantly lower than when the total amount of ethylene oxide is mixed with the ammonia at one location. With this procedure it is not necessary to have high proportions of water in the feed in order that the heat of reaction may be removed in the form of hot reaction product. The water included in the feed has to be removed from the reaction product by distillation. The process of the invention therefore brings about an appreciable energy saving. The amount of water added in the process of the invention is just sufficient for the residence time of the reaction to be long enough to ensure complete conversion of the ethylene oxide used.

Heat is generally also removed by the ammonia which is used in excess. In the process of the invention it is possible to use a lower ratio of ammonia to ethylene oxide without change in the ratio of water to ammonia without raising the maximum reaction temperature. This is because the separate introduction of ethylene oxide at a plurality of locations also distributes the energy over a longer proportion of the tubular reactor. The further decrease in the molar ratio of ammonia to ethylene oxide increases the flexibility of the production of the individual ethanolamines (monoethanolamine, diethanolamine, triethanolamine).

The addition of ethylene oxide in a plurality of portions lowers the maximum reaction temperature. The reaction product can be distilled to yield pure products (monoethanolamine, diethanolamine, triethanolamine) which do not change their color on storage.

The reduction in the maximum reaction temperature makes it possible to reduce the reaction pressure without incurring diphasicness in the reactor. Cost saving in capital expenditure and lower energy consumption for the compression of the feed materials are the result.

A further advantage of the process according to the invention is that adding the ethylene oxide at a plurality of locations makes it possible to influence the distribution of the ethanolamines produced—monoethanolamine:diethanolamine:triethanolamine. As stated above, increasing the molar excess of ammonia to ethylene oxide increases the proportion of monoethanolamine product in the reaction mixture. High monoethanolamine levels require a high excess of ammonia. The unconverted ammonia is generally distilled off or vaporized by decompression. The process of the invention makes it possible to produce an ethanolamine mixture with a relatively high monoethanolamine content without changing the ratio of ammonia to ethylene oxide. If ammonia and ethylene oxide are used in a molar ratio of 7.6 (and the ethylene oxide is introduced at one location), the mixture obtained contains 52.6% by weight of monoethanolamine, 33.9% by weight of diethanolamine and 13.5% by weight of triethanolamine. If at the same molar ratio of ammonia to ethylene oxide the ethylene oxide required is split into two portions (1st ethylene oxide feed: 60% of the ethylene oxide, 2nd ethylene oxide feed: 40% of the ethylene oxide), the ethanolamine mixture obtained contains 58.7% by weight of monoethanolamine, 30.6% by weight of diethanolamine and 10.7% by weight of triethanolamine. If the entire ethylene oxide and the ammonia are mixed at one location upstream of the reactor, the monoethanolamine content of 58.7% by weight is obtained with a molar ratio of ammonia to ethylene oxide of 9.6. The process of the invention makes it possible to increase the proportion of monoethanolamine without changing the molar ratio of $NH_3$: ethylene oxide. However, the same monoethanolamine level can also be achieved with a lower excess of ammonia. This leads to a significant energy saving, since less ammonia and water have to be distilled off.

Monoethanolamine, diethanolamine and triethanolamine are useful as solvents or as bases for organic reactions.

EXAMPLES

Example 1

A tubular reactor (length: 1500 m, internal diameter: 125 mm) is used to react ethylene oxide and ammonia in aqueous solution (87% by weight of ammonia) at 90 bar. Each of the tubes of the tubular reactor has a jacket. The first 100 m of the tubular reactor can be heated via the jacket. The remaining 1400 m are cooled via the jacket. The cooling can be adjusted in such a way that a prescribed maximum reaction temperature is not exceeded.

Suitable pumps are used to compress the ammonia in aqueous solution to the reaction pressure. Ethylene oxide is likewise compressed to the reaction pressure. The two streams are mixed directly upstream of the reactor. It is possible to introduce streams of the ethylene oxide into the reactor at various locations along the length of the reactor. The reactor exit stream is decompressed at the downstream end of the reactor. The unconverted ammonia and the water are distilled off. The ethanolamine mixture remaining behind is usually worked up by distillation for the monoethanolamine, diethanolamine and triethanolamine.

10 t/h of $NH_3$ in aqueous solution ($NH_3$ content=87% by weight) were mixed with ethylene oxide at 20° C. and introduced into the reactor. Ethylene oxide was split. One part was mixed with $NH_3$ in aqueous solution directly upstream of the reactor and introduced into the reactor (1st feed), while the other part of the ethylene oxide was introduced into the reactor about 500 m downstream of the upstream end of the reactor (2nd feed).

| Run 1: | 1st feed = | 5900 kg/h |
|---|---|---|
|        | 2nd feed = | 0 kg/h |
| Run 2: | 1st feed = | 5300 kg/h |
|        | 2nd feed = | 600 kg/h |
| Run 3: | 1st feed = | 4700 kg/h |
|        | 2nd feed = | 1200 kg/h |
| Run 4: | 1st feed = | 4100 kg/h |
|        | 2nd feed = | 1800 kg/h |
| Run 5: | 1st feed = | 3500 kg/h |
|        | 2nd feed = | 2400 kg/h |

TABLE A

|  | Run 1 | Run 2 | Run 3 | Run 4 | Run 5 |
|---|---|---|---|---|---|
| Max. reaction temperature | 147° C. | 144° C. | 141° C. | 139° C. | 136° C. |
| Weight % in ethanolamine mixture | | | | | |
| Monoethanolamine | 52.7 | 54.6 | 55.8 | 57.1 | 58.7 |
| Diethanolamine | 33.9 | 32.9 | 32.6 | 31.6 | 30.6 |
| Triethanolamine | 13.4 | 12.5 | 11.9 | 11.3 | 10.7 |

Example 2

Reactor and procedure as in Example 1. 26 t/h of $NH_3$ in aqueous solution ($NH_3$ content=87% by weight) were mixed with ethylene oxide at 20° C. and introduced into the reactor. Ethylene oxide was split. One part was mixed with $NH_3$ in aqueous solution directly upstream of the reactor and introduced into the reactor (1st feed), while the other part of the ethylene oxide was introduced into the reactor about 500 m downstream of the upstream end of the reactor (2nd feed).

| Run 1: | 1st feed = | 6500 kg/h |
|---|---|---|
|        | 2nd feed = | 0 kg/h |
| Run 2: | 1st feed = | 5850 kg/h |
|        | 2nd feed = | 650 kg/h |
| Run 3: | 1st feed = | 5200 kg/h |
|        | 2nd feed = | 1300 kg/h |
| Run 4: | 1st feed = | 4550 kg/h |
|        | 2nd feed = | 1950 kg/h |
| Run 5: | 1st feed = | 3900 kg/h |
|        | 2nd feed = | 2600 kg/h |

TABLE B

|  | Run 1 | Run 2 | Run 3 | Run 4 | Run 5 |
|---|---|---|---|---|---|
| Max. reaction temperature | 147° C. | 144° C. | 141° C. | 139° C. | 136° C. |
| Weight % in ethanolamine mixture |  |  |  |  |  |
| Monoethanolamine | 58.1 | 59.3 | 60.6 | 61.8 | 63.0 |
| Diethanolamine | 31.6 | 30.8 | 30.0 | 29.8 | 29.6 |
| Triethanolamine | 10.3 | 9.9 | 9.4 | 8.4 | 7.4 |

We claim:

1. A process for producing mixtures of mono-, di- and triethanolamine by reacting ammonia and ethylene oxide in a cooled tubular reactor at temperatures from 110° to 160° C. and at pressures from 50 to 120 bar, the molar ratio of ammonia to ethylene oxide being from 1:1 to 100:1 while using ammonia in the form of a 60 to 99.99% strength aqueous solution, in which the reaction is carried out by the steps comprising:

initially introducing only part of the ethylene oxide mixed with ammonia at the upstream end of the reactor; and subsequently adding from 1 to 80% of the total ethylene oxide in from one to ten aliquots over from 10 to 70% of the total length of the tubular reactor.

2. A process for producing mixtures of mono-, di- and triethanolamine as claimed in claim 1, wherein from 5 to 60% of the ethylene oxide is added in from one to eight aliquots over from 20 to 60% of the total length of the tubular reactor.

3. A process for producing mixtures of mono-, di- and triethanolamine as claimed in claim 1, wherein from 10 to 50% of the ethylene oxide is added in from one to six aliquots over from 25 to 50% of the total length of the tubular reactor.

4. A process for producing mixtures of mono-, di- and triethanolamine as claimed in claim 1, wherein the reaction is carried out at temperatures from 120° to 150° C.

5. A process for producing mixtures of mono-, di- and triethanolamine as claimed in claim 1, wherein the reaction is carried out at pressures from 60 to 110 bar.

6. A process for producing mixtures of mono-, di- and triethanolamine as claimed in claim 1, wherein the reaction is carried out at pressures from 75 to 100 bar.

7. A process for producing mixtures of mono-, di- and triethanolamine as claimed in claim 1, wherein ammonia is used as a from 65 to 99% strength aqueous solution.

8. A process for producing mixtures of mono-, di- and triethanolamine as claimed in claim 1, wherein ammonia is used as a from 70 to 95% strength aqueous solution.

9. A process for producing mixtures of mono-, di- and triethanolamine as claimed in claim 1, wherein ammonia is used as a from 75 to 90% strength aqueous solution.

10. A process for producing mixtures of mono-, di- and triethanolamine as claimed in claim 1, wherein ammonia and ethylene oxide are used in a molar ratio from 3:1 to 50:1.

* * * * *